(12) United States Patent
Zalevsky et al.

(10) Patent No.: US 10,931,881 B2
(45) Date of Patent: Feb. 23, 2021

(54) SAMPLE INSPECTION UTILIZING TIME MODULATED ILLUMINATION

(71) Applicant: ContinUse Biometrics Ltd., Tel Aviv (IL)

(72) Inventors: Zeev Zalevsky, Rosh HaAyin (IL); Ran Califa, Givataym (IL); Zeev Markman, Bet-Dagan (IL); Yevgeny Beiderman, Tel Aviv (IL)

(73) Assignee: CONTINUSE BIOMETRICS LTD., Tel Aviv (IL)

( * ) Notice: Subject to any disclaimer, the term of this patent is extended or adjusted under 35 U.S.C. 154(b) by 0 days.

(21) Appl. No.: 16/575,944

(22) Filed: Sep. 19, 2019

(65) Prior Publication Data

US 2020/0099839 A1    Mar. 26, 2020

Related U.S. Application Data

(60) Provisional application No. 62/733,802, filed on Sep. 20, 2018.

(51) Int. Cl.
| | |
|---|---|
| *H04N 5/235* | (2006.01) |
| *G01B 11/25* | (2006.01) |
| *A61B 5/00* | (2006.01) |

(52) U.S. Cl.
CPC ......... *H04N 5/2351* (2013.01); *G01B 11/254* (2013.01); *H04N 5/2352* (2013.01); *H04N 5/2353* (2013.01); *H04N 5/2354* (2013.01)

(58) Field of Classification Search
CPC .. H04N 5/2351; H04N 5/2352; H04N 5/2353; H04N 5/2354; G01B 11/254;
(Continued)

(56) References Cited

U.S. PATENT DOCUMENTS

| 2014/0036272 A1* | 2/2014 | Nadkarni | A61B 5/0066 |
| | | | 356/450 |
| 2019/0159701 A1* | 5/2019 | Beiderman | A61B 5/1103 |

(Continued)

FOREIGN PATENT DOCUMENTS

| WO | 2017/191639 A1 | 11/2017 |
| WO | 2017/203525 A1 | 11/2017 |

OTHER PUBLICATIONS

Zeev Zalevsky: "Temporally masked camera readout technique for obtaining an invariance to platform vibration distortions", Optical Engineering, vol. 44, No. 1, Jan. 1, 2005.

(Continued)

*Primary Examiner* — Susan E. Hodges
(74) *Attorney, Agent, or Firm* — Browdy and Neimark, PLLC

(57) ABSTRACT

A system and corresponding method are presented. The system includes an illumination unit including at least one light source configured for emitting coherent illumination of one or more selected wavelength ranges having selected illumination modulation pattern and for directing the coherent illumination onto one or more selected inspection regions; and a collection unit including at least one detector array and imaging optical arrangement configured for collecting interacting light from the one or more selected inspection regions and for generating corresponding one or more sequences of image data pieces at selected sampling rate. The image data pieces are indicative of secondary speckle patterns formed in collected interacting light. The illumination modulation pattern is selected for increasing temporal bandwidth collection of speckle patterns associated with temporal shifts in the one or more inspection regions.

16 Claims, 11 Drawing Sheets

(58) Field of Classification Search
CPC .......... G01B 9/02014; G01B 9/02011; G01B 9/02094; A61B 5/0059; A61B 5/7257; A61B 5/7203; A61B 5/7228
USPC .......................................................... 348/138
See application file for complete search history.

(56) References Cited

U.S. PATENT DOCUMENTS

2019/0212124 A1* 7/2019 Zalevsky .......... G01B 9/02094
2019/0274560 A1* 9/2019 Zalevsky .......... A61B 5/02416

OTHER PUBLICATIONS

Chang Robert W: "Synthesis of band-limited orthogonal signals for multichannel data transmission", Bell System Technical Journal, AT and T, Short Hills, NY, US, vol. 45, No. 10, Dec. 1, 1966.

* cited by examiner

SAMPLE INSPECTION UTILIZING TIME MODULATED ILLUMINATION

TECHNOLOGICAL FIELD

The present invention relates for optical inspection techniques, and more specifically to motion detection techniques enabling sampling and monitoring motion of a tissue with improved signal to noise ratio for high frequency variations and sampling bandwidth.

BACKGROUND

Optical monitoring enables non-invasive inspection of various samples, being biological tissue or other samples. Various optical monitoring techniques enable motion detection within a sample and recognition of one or more sample parameters. Such optical monitoring techniques may thus be used as essential tools in a broad range of applications. Moreover, optical monitoring provides especially great significance in biomedical utilities for measuring physiological parameters of a human body, for example monitoring heart rate, breathing, blood pressure, etc. by allowing non-invasive monitoring.

Speckle-based monitoring techniques enable detection of vibrations and movement of tissue with high spatial resolution. For example, such techniques can detect heart beats of a subject from large distance and through clothes. These speckle-based techniques generally utilize monitoring time variation of patterns formed by secondary speckles generated due to self-interference of light components reflected and/or scattered from a surface of the sample. Movement and changes in orientation of the surface cause corresponding variations in the detected patterns, enabling highly sensitive monitoring.

GENERAL DESCRIPTION

As mentioned above, speckle-based monitoring techniques enable optical inspection using monitoring of variations in secondary speckle patterns. Such secondary speckle patterns may be formed in coherent light reflected from one or more inspection regions. Generally, one or more regions of a sample (herein referred to as inspection regions) are illuminated by one or more coherent light beams. The light returning from, or transmitted through, the illuminated region is collected by one or more imaging units generating image data pieces associated with secondary speckle patterns that are formed in the collected light. To this end, the imaging unit(s) may be configured for focused or defocused imaging of the inspection. More specifically, in some configurations the imaging unit is configured for imaging of an optical plane located at an intermediate plane between the inspection region and the imaging module, and the collected speckle patterns are processed by determining spatial correlations between them. In some other configurations, the imaging unit is configured to be in focus with respect to the inspection region, and the collected speckle patterns are processed by determining contrast or statistical variations between them. The imaging unit is thus operable for generating one or more sequences of image data pieces at a selected sampling rate, where each image data piece is indicative of an image of the inspection region (being in-focus or defocused) and comprising corresponding speckle pattern of interacting light, i.e. light interacting with one or more of the inspection regions being back-scattered from the inspection region or transmitted through medium of the inspection region. More specifically, the image data pieces are each indicative of one or more self-interference patterns formed by light components scattered from the inspection region, generally known as secondary speckle patterns.

There is a need in the art for an optical inspection system and corresponding monitoring technique, enabling monitoring one or more time-varying features at given sampling rate while improving collection of the temporally varying signal. Generally, the image data (or a general signal) is collected in a selected sampling rate, and where each frame is captured with a selected exposure time. As known, the sampling rate set the maximal temporal frequency that can be detected in the collected data in accordance with Nyquist criteria. Additionally, the finite exposure time associated with each frame performs integration of the collected data (speckle pattern) during the exposure time and act as low pass filter on the collected signal. The present technique utilizes selected illumination modulation, as described in more detail below, for improving signal quality associated with at least one of low-pass filter associated with integration during collection of each frame (exposure time) and bandwidth of temporal frequencies of signal that can be collected based on Nyquist criteria.

To this end, the present technique utilizes an optical inspection and monitoring system. The system may comprise an illumination unit and a collection unit and may also comprise a control unit adapted for operating the optical inspection system and processing collected data as described herein below. The illumination unit comprises at least one light source configured for emitting coherent illumination of one or more selected wavelength ranges having selected illumination modulation pattern (generally temporal modulation pattern), and for directing the illumination onto one or more selected inspection regions. The collection unit comprises at least one detector array and imaging optical arrangement positioned and operated for collecting interacting light, i.e. light interacting with (being back-scattered from or transmitted through) the one or more inspection regions and for generating corresponding one or more sequences of image data pieces at selected sampling rate. Generally, the image data pieces are associated with secondary speckle patterns formed in light components back scattered from or transmitted through the inspection region.

According to the present technique, the pulse modulation pattern is selected for increasing temporal resolution and/or bandwidth of monitoring. To this end the pulse modulation pattern may be selected to increase signal to noise ratio of high temporal frequency features within each of said image data pieces. More specifically, such pulse modulation pattern is selected to eliminate, or at lease significantly reduce the low-pass filter effect of the integration time (exposure time) associated with collection of each frame. Alternatively, the illumination modulation pattern may be selected to increase temporal frequency bandwidth over that provided by the sampling rate. In these configurations, the illumination modulation pattern may be selected in accordance with spectral components as described in more detail further below.

As indicated, the present technique utilizes temporal illumination modulation pattern to provide signal collection to improve signal to noise ratio (SNR) for high frequency variations of the inspected features. The present technique overcomes sampling limitations associated with operation of the collection unit (including e.g. camera) at a selected exposure time, while improving SNR for detection of data having frequency that is relatively high and may be blurred due to the exposure time. To this end, the present technique utilizes proper modulation of a sampling window, associated with collection of image data by modulation the illumination providing the collected signal. More specifically, the present technique utilizes modulation of sampling window profile associated with collection of each image data piece, to allow improved collection of high temporal frequencies data within the sequence of image data pieces. More specifically, the present technique eliminates, or at least significantly reduces smeared feature within images, associated with variations in the collected speckle pattern that occur during exposure (integration) time of the imaging modules or the detector thereof.

Thus, the present invention provides a system adapted for monitoring of one or more regions of a sample. The system comprises an illumination unit configure for emitting coherent illumination beam of one or more selected wavelength ranges onto one or more selected inspection regions on a sample, and a collection unit configured and operable for collecting at least one sequence of image data pieces associated with interacting light (light components being back-scattered from or transmitted through) from said one or more inspection regions. The image data pieces are associated with respective speckle patterns formed by light interference due to scattering from the inspected region on the sample. The system may further comprise a control unit configured for receiving and processing said at least one sequence of image data pieces for determining data about one or more parameters of the sample.

According to some embodiments of the present technique, the illumination unit is configured to modulate the coherent illumination beam with a selected pulsed modulation pattern. The modulation pattern of the illumination beam is selected to vary sampling windows of the system, thus enabling improved sampling of high temporal frequency events/features. The improved sampling is generally in the meaning of improved signal to noise ratio (SNR) of spatial distribution of the collected speckle patterns. The pulse modulation of the illumination pattern typically includes one or more instances in which the amplitude of illumination is zero. This forms an effective pause during each sampling instance, or during collection of each image data piece. To this end, the selected pulsed modulation pattern enables to increase spatial SNR for sampling of high temporal frequency events, by reducing and modulating integration time of the image data pieces, with respect to unmodulated integration time.

Typically, the modulated illumination pattern is temporally aligned with sampling windows of the collection unit. More specifically, operation of the collection unit for sampling the one or more sequences of image data piece and the illumination unit providing modulated illumination pattern are synchronized such that the pattern of illumination does not changed beyond a selected threshold between collection times of different images.

Generally, the use of suitably modulated illumination pattern enables improved sampling of time varying signals from a selected sample. This improvement may generally resolve the issue formed by non-ideal sampling bandwidth of (generally) any camera/imager unit. In some configurations the use of modulated illumination pattern as described herein may provide 40% and, in some configuration even 50% bandwidth improvement over the sampling bandwidth provided by given camera unit.

According to some additional embodiments, the present invention utilizes illumination modulation pattern selected for improving bandwidth of signal collection. To this end, the present technique utilizes digitization of the frequencies of the illumination pattern, due to the sampling rate (providing digitization of the sapling). This digitization forms a plurality of spectral slots in the temporal frequency domain. To this end, the illumination modulation pattern provides orthogonal encoding of the spectral slots of the patterned illumination. While, the encoding of the illumination pattern is determined in accordance with the spectral slots associated with sampling rate and digitalization of the frequency domain of the pattern. More specifically, the discrete sampling rate of the collection unit separates the collected signal into digitized spectral slots, as well as defining maximal temporal frequency for signal detection. The present technique utilizes convolution orthogonal encoding of the different temporal spectral slots for enabling reconstruction of the temporal signal data with increased temporal spectral width as compared to that defined by the sampling rate. This technique is directed at improving sampling bandwidth over that allowed by the sampling rate of a given camera unit used. In some configurations the use of orthogonal encoding of spectral illumination slots may allow sampling with bandwidth that is three or four times with respect to that given by sampling rate of a camera unit used.

Thus, according to one broad aspect, the present invention provides a system comprising:
an illumination unit comprising at least one light source configured for emitting coherent illumination of one or more selected wavelength ranges having selected illumination modulation pattern, and for directing said illumination onto one or more selected inspection regions;
a collection unit comprising at least one detector array and imaging optical arrangement configured for collecting interacting light, being light components interacting with the one or more inspection regions (being back scattered from or transmitted through) and for generating corresponding one or more sequences of image data pieces at selected sampling rate, said image data pieces being indicative of secondary speckle patterns formed in collected light after interaction with the inspection region; wherein said illumination modulation pattern is selected for increasing temporal bandwidth collection of speckle patterns associated with temporal shifts in said one or more inspection regions.

According to some embodiments, the said illumination modulation pattern may comprise a selected arrangement of pulses providing at least one instance of zero amplitude portion within exposure time of the collection unit for collection of a corresponding image data piece. Additionally or alternatively, the illumination modulation pattern may comprise pulse profile having repeating patterns comprises at least one zero intensity portion associated with exposure window of the collection unit. The repeating pattern may be aligned with sampling rate of said collection unit.

Additionally or alternatively, the illumination modulation pattern may comprise modulation of polarizing orientation of the coherent illumination directed toward said one or more selected inspection regions, said collection unit is configured and operable for collecting light of selected polarization orientation, thereby modulating collected light.

According to some embodiments, the at least one light source may be associated with at least one light modulation unit configured for modulating at least one of intensity and polarization of light emitted by the light source.

Generally, the illumination modulation pattern may comprise a binary sequence of ON and OFF illumination periods. Alternatively or additionally, the illumination modulation pattern may comprise an intensity variation of illumination having at least three intensity levels, providing at least one temporal instance having zero illumination within frame of light collection.

For example, the illumination modulation pattern may be of any one of the following formats: 5321, A85321, A8532111, 432111, 5322111, wherein hexadecimal digits in odd positions indicated length of ON period and hexadecimal digits in even positions indicate length of OFF period. It should however be noted that various additional modulation formats are known and these given modulation formats are brought herein as tested examples.

According to some embodiments, the imaging optical arrangement and at least one detector array of the collection unit may be positioned for generating defocused image with respect to the one or more selected inspection regions. Alternatively, the imaging optical arrangement and at least one detector array of the collection unit may be positioned for imaging of the one or more selected inspection regions in-focus.

According to some embodiments, the illumination modulation pattern may be characterized by a plurality of spectral slots associated with digitization by sampling rate of the collection unit, wherein said plurality of spectral slots are modulated to be orthogonal between them with respect to convolution operation. Generally, the orthogonality of the coding is determined prior to sampling of the signal. It should be noted that the illumination modulation pattern is temporal pattern, and that the spectral slots are in temporal frequency domain.

The system may comprise a control unit, the control unit comprises at least one processor and memory utility and is adapted for receiving said one or more sequences of image data pieces from the collection unit, determining at least one time-varying function indicative of variations between speckle patterns of different frames, said at least one time-varying function being indicative of variations of temporal features in the one or more inspection region.

The control unit may further be adapted for decoding said illumination modulation pattern, said decoding comprises: determining frequency representation of the collected signal, identifying first signal portion associated with maximal temporal frequency slot, utilizing prestored data on the illumination modulation pattern and decoding said first signal portion, identifying next signal portion associated with neighboring frequency slot, using orthogonality of the codes and prestored data on the illumination modulation pattern for decoding said next signal portion, maintaining said process for decoding the collected signal.

According to one other broad aspect, the present invention provides a system comprising:
  illumination unit comprising light source unit configured to provide coherent illumination of one or more wavelength ranges onto an inspection region, said light source unit provides selected illumination pattern;
  collection unit comprising optical imaging arrangement and detector array configured to collect defocused light reflected from the inspected region; and data analyzing unit configured for receiving input data associated with defocused image data from the collecting unit and for generating output data indicative of spatial frequencies of the image data from the inspection region.

According to yet another broad aspect, the present invention provides a method for use in monitoring a sample, the method comprising:
  (a) providing modulated pulsed illumination onto at least one inspection region on the sample, said modulated pulsed illumination comprises illumination of at least one wavelength range carrying temporal modulation;
  (b) collecting interacting light, being light interacting with (being back-scattered from or transmitted through) said at least one inspection regions and generating at least one sequence of image data pieces associated with speckle patterns formed in the interacting light;
  wherein said modulated pulsed illumination is configured increasing signal to noise ratio of high temporal frequency features within each of said image data pieces.

According to some embodiments, the modulated illumination may be in the form of pulsed modulated illumination comprising pulse train profile having repeating patterns, comprising at least one zero intensity portion associated with exposure time for collection of light for generating said image data pieces, said repeating pattern being aligned with said selected sampling rate.

The modulated illumination may comprise modulation of polarizing orientation of the coherent illumination directed toward said sample, and wherein collection of interacting light comprises filtering light of selected polarization orientation, thereby modulating collected light.

According to some embodiments, the modulated illumination comprises a binary sequence of ON and OFF illumination periods. Alternatively, the modulated illumination may comprises an intensity variation of illumination having at least three intensity levels, providing at least one temporal instance having zero illumination within frame of light collection.

According to some embodiments, collecting the interacting light from said at least one inspection region may comprise collecting defocused images with respect to the one or more inspection regions.

According to some embodiments, collecting the interacting light from said at least one inspection region may comprise collecting in-focus images with respect to the one or more inspection regions.

According to some embodiments, the modulated illumination may be characterized by a plurality of spectral slots associated with digitization by sampling rate of the collection unit, wherein said plurality of spectral slots are modulated to be orthogonal between them with respect to convolution operation.

The method may further comprise receiving said one or more sequence of image data pieces, determining variations between speckle patterns of different frames and determining at least one time-varying function indicative of variations of temporal features in the one or more inspection region.

The method may further comprising determining Frequency representation of the collected signal, identifying first signal portion associated with maximal frequency slot, utilizing prestored data on the illumination modulation pattern and decoding said first signal portion, identifying next signal portion associated with neighboring frequency slot, using orthogonality of the codes and prestored data on the illumination modulation pattern for decoding said next signal portion, repeating said process for decoding the collected signal.

According to yet another broad aspect, the present invention provides a method for use in monitoring a sample, the method comprising determining one or more spectral slots K of signal collection including a maximal spectral slot and spectral slot width $\Delta\mu$; selecting first encoding pattern for the spectral slots K and providing measured signal $S_L(\alpha)$ being null for $S_K(\mu)$ and $S_{K+1}(\mu)$, while said measured signal $S_{K-1}(\mu)$ is non-null; utilizing said first encoded pattern and determining a second orthogonal encoded pattern for spectral slot K−1; repeating said selection for determining orthogonal encoding patterns for K spectral slots for providing signal sampling at spectral width Δμ.

According to yet another broad aspect, the present invention provides a system comprising:

illumination unit comprising at least one light source configured for emitting coherent illumination of one or more selected wavelength ranges and pattern modulator configured for applying selected modulation patterns to light emitted from the light source and for directing said illumination onto one or more selected inspection regions; collection unit comprising at least one detector array and imaging optical arrangement configured for providing defocused images of the one or more selected inspection regions onto said detector array, and for collecting one or more sequences of image data pieces at selected sampling rate; and a control unit comprising at least one processor configured for operating said illumination unit and for receiving and processing data indicative of one or more sequences of image data pieces received from the collection unit, said at least one processor being configured for determining one or more spectral slots K of signal collection including a maximal spectral slot and spectral slot width Δμ; selecting first encoding pattern for the spectral slots K and providing measured signal $S_L(\mu)$ being null for $S_K(\mu)$ and $S_{K+1}(\mu)$, while said measured signal $S_{K-1}(\mu)$ is non-null; utilizing said first encoded pattern and determining a second orthogonal encoded pattern for spectral slot K−1; repeating said selection for determining orthogonal encoding patterns for K spectral slots for providing signal sampling at spectral width Δμ.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

As indicated above, the present technique utilizes optical monitoring of parameters from one or more inspection regions on a sample using selected modulation of illumination of the inspection regions. The illumination modulation is selected to provide improved monitoring of temporally varying feature. Certain selected illumination modulation patterns are used for improved monitoring of high frequency varying features of the inspection regions, i.e. removing, or at lease significantly reducing low-pass filter effects of exposure/integration time. To this end the present technique utilizes temporal blocking function overlapping with exposure/integrating time for collection of image data from one or more inspection regions, thereby enhancing signal to noise ratio of high frequency portions of the inspected features.

Figure 1:
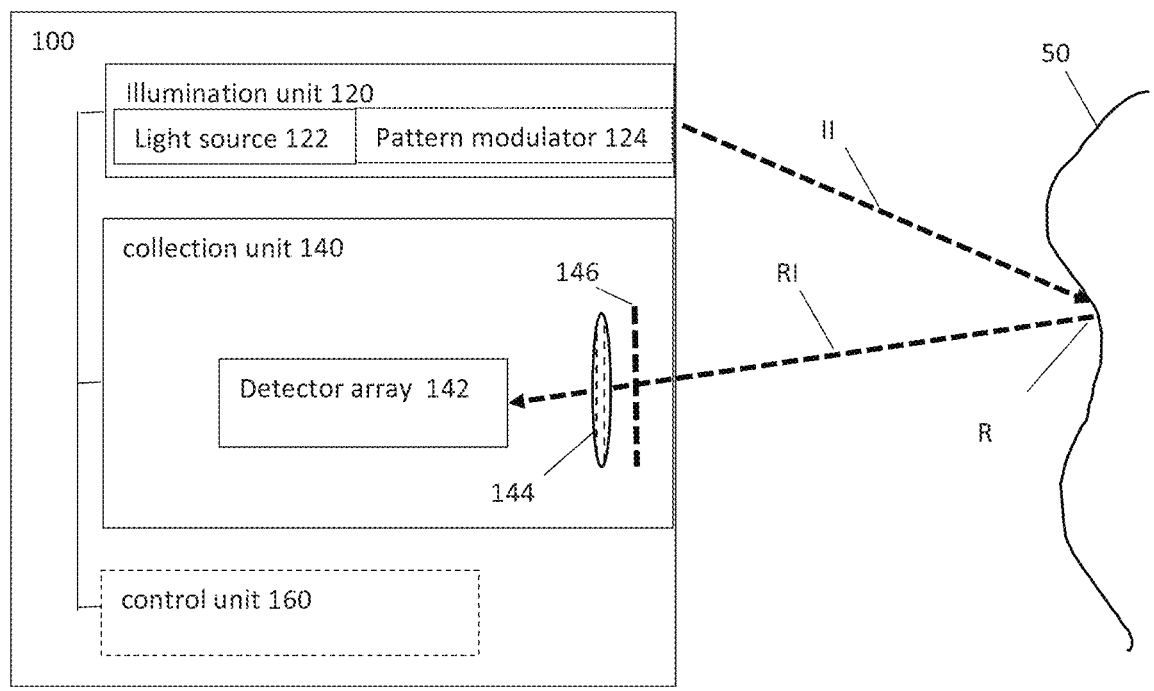
FIG. 1 schematically illustrates an inspection system according to some embodiments of the present technique.

Reference is made to FIG. 1 schematically illustrating a system 100 according to some embodiments of the present technique. The system 100 includes an illumination unit 120 and a collecting unit 140 and is configured for monitoring one or more inspection regions R on the sample 50.

The illumination unit 120 includes at least one light source 122 (e.g. at least one laser unit) configured and operable to illuminate one or more inspection regions R on the sample 50 using one or more coherent light beams, one light beam II is exemplified in FIG. 1. The light beam II is coherent light beam of a one or more selected wavelength ranges. The illumination unit 120 may further include a pattern modulator 124 configured for modulating a temporal pattern of illumination emitted from the light source 122 in accordance with the preset technique as described herein. The pattern modulator 124 may be formed as an optical patterning unit (e.g. aperture modulator selectively modulating light intensity or polarization), or electronic modulator adapted for modulating operation of the light source 122 for emitting the one or more coherent light beams. The temporal pattern of illumination may be associated with intensity and/or polarization pattern of the emitted light beam with a selected temporal cycle. More specifically, the pattern modulator 124 may be separate from the light source 122 and configured for receiving input illumination from the light source 122 and for modulating the illumination beam. Additionally or alternatively, the light source 122 itself may include an integral pattern modulator 124 enabling intensity and/or polarization modulation. Accordingly, the pattern modulator 124 is shown herein as an exemplary module indicating illumination pattern of the light source 122. Thus, the illumination unit 120, using the at least one light source 122 is configured for providing one or more light beam II having a selected pulsed temporal modulation pattern and directing the light beam II onto one or more inspection regions R on the sample 50.

The collecting unit 140 includes at least one detector array 142 and corresponding at least one optical arrangement 144, and is configured for collecting interacting light, i.e. light RI being back-scattered from (or transmitted through) the at least one inspection region R and generating at least one sequence of image data pieces associated with speckle patterns formed in the returning light RI. It should be noted, and is indicated above, that substantially similar technique is useful with collection of light components transmitted through the medium of the inspection region. In some configurations, the collecting unit 140 may also include a polarization analyzer unit 146, located upstream (as shown in FIG. 1) or downstream of the optical arrangement 144, or between optical elements of the optical arrangement. The polarization analyzer may be used for improving SNR of collected image data, either when used with polarization modulation or when using polarized illumination with intensity modulation thereof. The optical arrangement 144 and the detector array 142 may be positioned to provide defocused imaging of the inspection region R for collecting image data piece including secondary speckle patterns formed by self-interference of light reflected/scattered from the region R. Alternatively, the optical arrangement 144 and detector array 142 may be positioned for imaging the inspection region (i.e. in-focus imaging) for collection of speckle pattern in transmitted or back-scattered light. The collection unit 140 may be operate for collecting image frames at a selected sampling rate and selected exposure time window for each image. Generally, when using a plurality of two or more light beams II for illuminating corresponding two or more regions on the sample 50, a single collection unit 140 may be used for generating image data pieces such that each image includes two or more speckle patterns associated with the two or more regions R. Alternatively, a plurality of two or more collection units 140 may be used for collecting two or more sequences of image data pieces associated with the two or more inspection region.

The modulation pattern of the illumination II may be selected in accordance with sampling rate (frame rate) and exposure window time of the collection unit 140 for providing increased signal to noise ratio (SNR) for events/features having relatively high frequency. More specifically, the detector array 142 is operated for collecting image data by integrating input light collected during exposure time thereof such that data in the resulting image frames relates to integrated light intensity along exposure time for each image pixel. Changes in the collected speckle pattern occurring within the exposure time result in smearing of the speckle patterns collected in each image frame. This effect is similar to the result of photographing a fast-moving car using a camera with long exposure time. The modulation of the illumination pattern is selected to shorten the effective exposure time, e.g. splitting the exposure time into two or more portions, resulting in increased SNR as the fast-occurring variations are sampled during shorter integration time. This is provided by modulating intensity of illumination and/or modulating polarization of the illumination beam while collecting interacting light (being back-scattered from or transmitted through) from the inspection region R with specific polarization (e.g. linear polarization of certain selected angle).

The modulation of illumination pulses is selected to provide one or more temporal instances within exposure time of the frames, where the collected illumination is zero. Generally, modulating emission pattern of the laser (e.g. using a shutter) or varying polarization of the illumination beam, and collecting light of specific polarization orientation, may vary collected intensity. When such modulation is provided with suitable pattern, light collection within the frames may be modulated as described herein below.

Additionally, the system 100 may include, or be associated with, a control unit 160 configured for controlling operation of the illumination unit 120 and collection unit 140 and for receiving input data associated with the at least one sequence of image data pieces collected by the collection unit 140. The control unit 160 may further be configured for processing the collected image data pieces for determining one or more parameters of the sample. The control unit 160 may be integral with system 100 or external thereto. In some configurations system 100 may include a control unit 160 for controlling operation thereof, while providing output data indicative of the collected image data pieces to an external computing system for processing and determining parameters of the sample 50. Generally, the control unit 160 may be configured as a computing unit including one or more processors, storage utility and input/output communication ports not specifically shown in FIG. 1. The control unit 160 may be connectable to the illumination unit 120 for operating the light source 122 and the pattern modulator 124 thereof e.g. for selecting and synchronizing modulation of the illumination directed at the inspection region R. Additionally, the control unit may be connectable to the collection unit 140 for operating the collection unit to collect image data pieces at selected sampling rate and selected exposure time, and for receiving collected image data for storing, processing and/or transmitting to remote location for storing and/or processing.

Figure 2A:
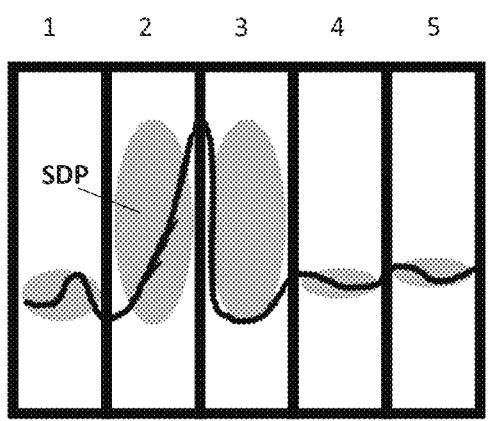
FIGS. 2A and 2B exemplify concept of signal collection using time varying collection windows separating the signal into frames having certain exposure times.
Figure 2B:
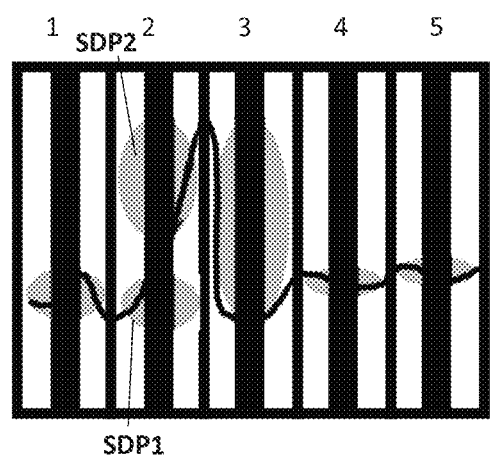

The effect of modulation of the collection/integration time according to the present technique is exemplified in FIGS. 2A and 2B illustrating the collection of a time varying functions into frames having certain exposure time. FIG. 2A illustrates conventional exposure windows integrating input light throughout the exposure period. FIG. 2B illustrates a modulated exposure window having dark period within the exposure time. FIGS. 2A and 2B clearly show that the general trend of collected data is similar. However, relating to section 2 of the collected frames, the conventional collection technique shows smeared data point SDP, while the modulated collection scheme exemplified in FIG. 2B shows two separated data points SDP1 and SDP2 associated with a common frame. Although certain time ambiguity may limit reconstruction of the signal, generally in accordance with Nyquist theorem, the signal intensity is increased with respect to noise resulting with smearing of the signal.

As indicated above, the control unit 160 may include data input and output utilities/modules, and one or more processors adapted for receiving and processing collected image data sequence and determining one or more selected parameters of the sample. Generally, when the image data pieces collected are defocused with respect to the inspection region, the processing may include determining correlations between speckle patterns in different (e.g. consecutive) image data pieces and accordingly, determining corresponding one or more time-correlation functions indicative of vibrations or movements of the one or more inspection regions R of the sample. Such vibrations may be indicative of heart rate, breathing, acoustic sound (e.g. speech, cardiac sounds etc.) or physical vibrations of the sample 50. In some configurations where the image data pieces are collected by the collection unit 140 being in-focus with respect to the inspection region, either by collected transmitted light or back-scattered light, the processing may include determining variations in contrast of the speckle patterns or spatial decorrelation statistics between speckle patterns.

The inventors of the present invention have conducted simulation and experiments for qualifying and validating the present technique. The Experimental verification was performed using Basler camera operated selectively at frame rates of 30, 60 and 120 fps, a sample formed by piezoelectric element carrying a surface plate was illuminated using unbranded simple 650 nm 5 mW continuous wave (CW) laser element. The above described technique is used for monitoring vibrations of a piezoelectric based sample. The sample was operated to provide tilt and small z-direction movement in a first test, and to provide z-direction movement with minor tilt is a second test. In both tests, the sample was illuminated with coherent light beam and light reflected from the sample was collected by the Basler camera at defocused configuration to provide image data pieces indicative of secondary speckle patterns in the reflected light. Movements of the piezoelectric based sample are driven by a signal generator (e.g. Tecktronix signal generator) supplying sinewave excitation to the piezoelectric element.

Movements of the piezoelectric sample were measured including tilt and small z-direction movement in one configuration, and z-direction movement and small tilt in another configuration. This non-ideal tilt and z-direction surface movements produce together harmonics in spectrum of surface variations that can be detected via monitoring of correlation between collected speckle patterns. The piezoelectric element was driven at sinewave frequencies of 20, 15, 5, 4, 3, 2, and 1 Hz for testing. The initial testing shows that waves of 5, 4, 3, 2, and 1 Hz produce harmonics with corresponding resolution steps suitable for inspection of high temporal frequency variation using the Basler camera.

Figure 3:
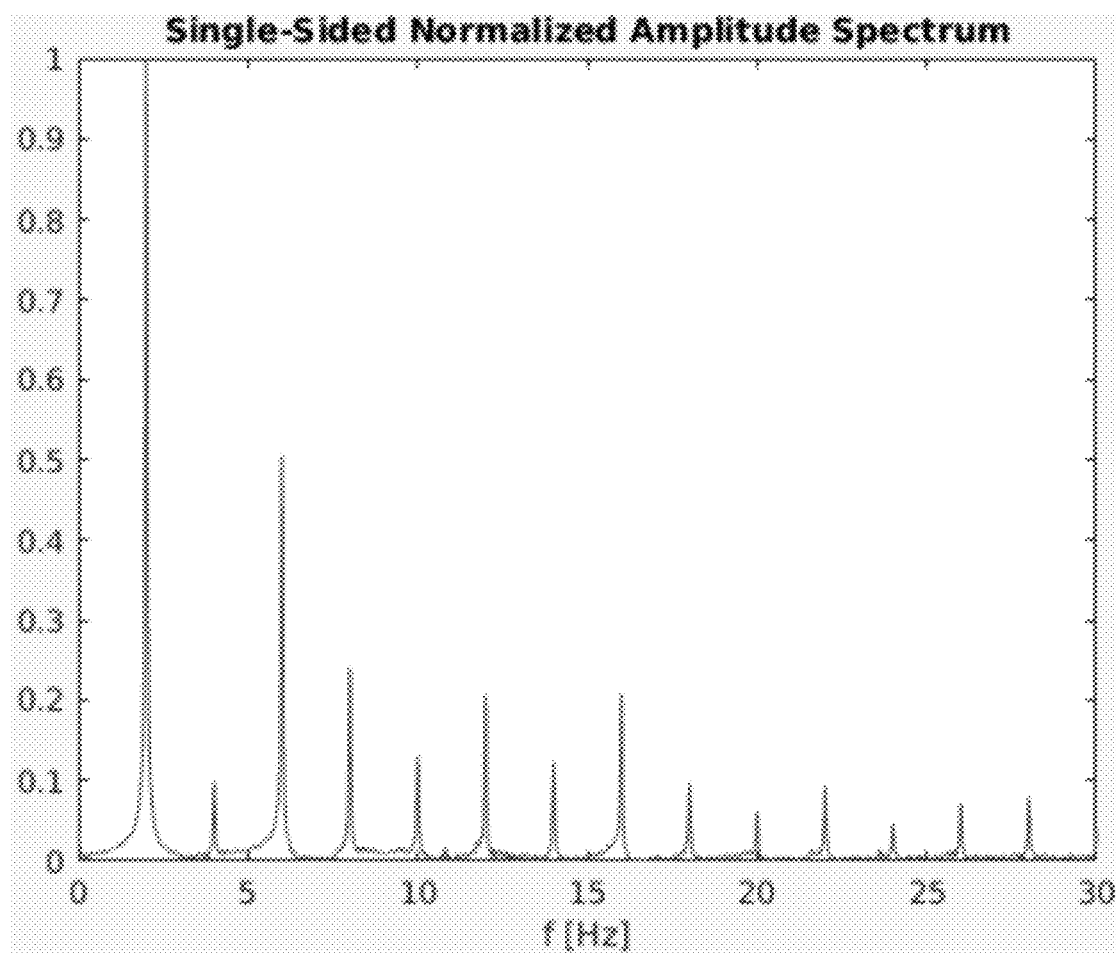
FIG. 3 exemplifies gain frequency curve of sample monitoring using CW illumination.

For simplicity, the majority of the following experimental data is based on excitation using 2 Hz sinewave. This excitation frequency generates high harmonics separated by 2 Hz step resolution shown in FIG. 3. As shown, the generated high harmonics provides a single-sided normalized amplitude spectrum, in which the gain (collected signal with respect estimates vibration amplitude) is higher for the lower frequency (2 Hz) and reduces with frequency increase.

Figure 4:
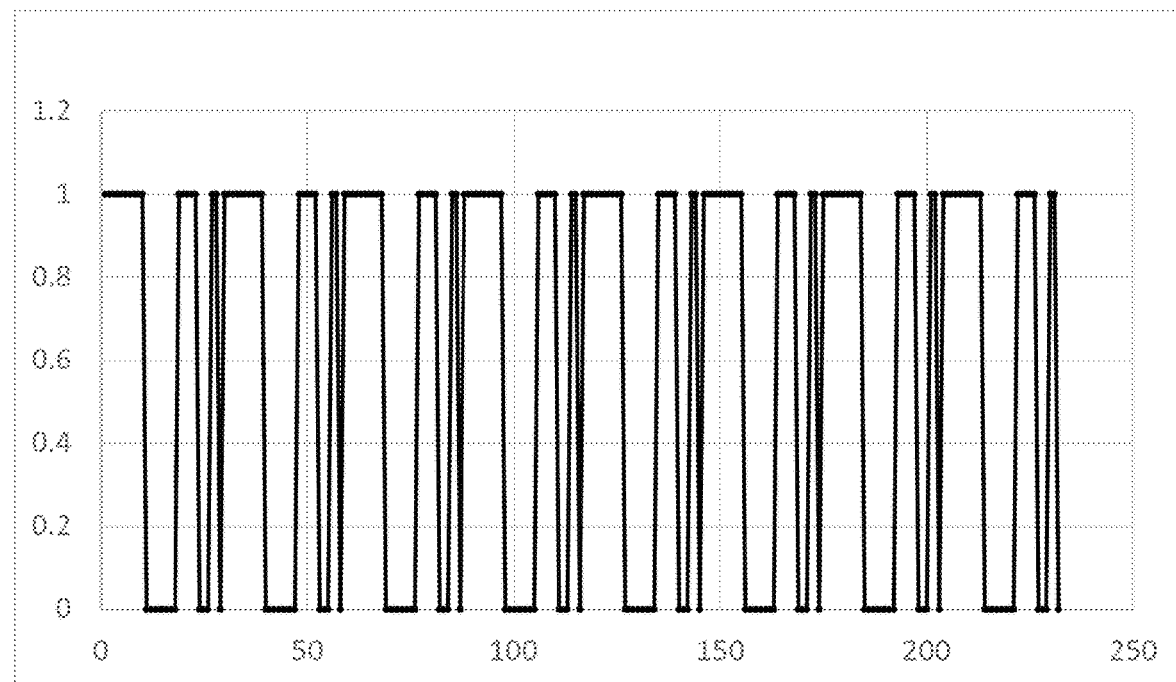
FIG. 4 exemplifies A85321 illumination pattern.

The tested illumination modulation patterns were selected in accordance with sampling rate of the camera as well as switching time of the laser light source. More specifically, the sequential pattern is formed of "ticks" of minimal time providing bit duration and selected in accordance with laser switching time. To overcome restriction of pattern synchronization to the start of each frame the sequential pattern (repeating of basic code) is formed with maximal velocity where minimal bit duration is limited by the laser switching time. For simplicity, each pattern is formed by a certain number of on ticks (in which the laser beam is on), following by a number of off ticks (in which the laser beam is off), an additional number of on tick etc. Such patterns were marked by selected pattern naming utilizing hexadecimal digits at odd positions indicate length of high level (ON) ticks and hexadecimal digits at even position stand for low-level (OFF) ticks. FIG. 4 exemplifies a pattern of repeated sequence A85321 formed by repeating sequence of 10 high ticks, 8 low, 5 high, 3 low, 2 high, 1 low.

Figure 5:
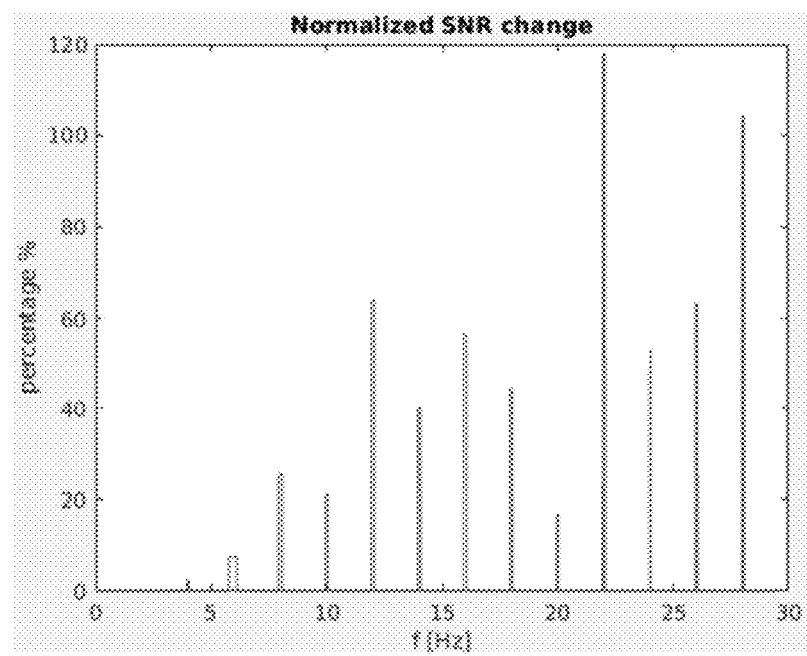
FIG. 5 shows normalized gain curve associated with signal inspection using the 5321-modulation pattern according to some embodiments of the present invention.
Figure 6:
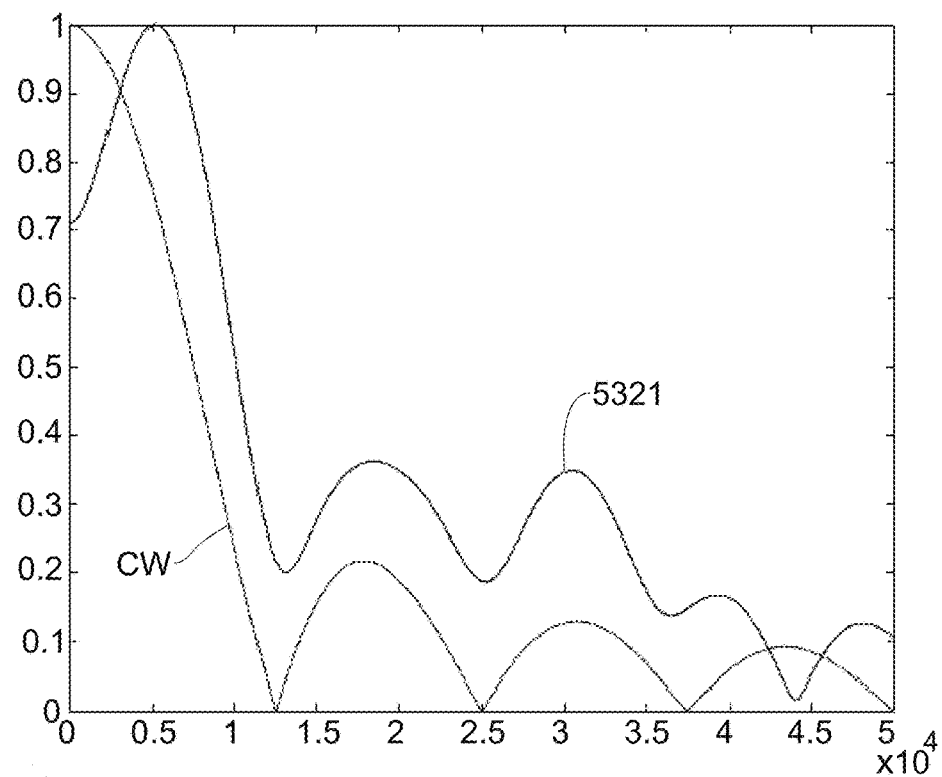
FIG. 6 shows mathematical calculation of normalized Sync function modulated by the 5321 pattern and by CW illumination.
Figure 7:
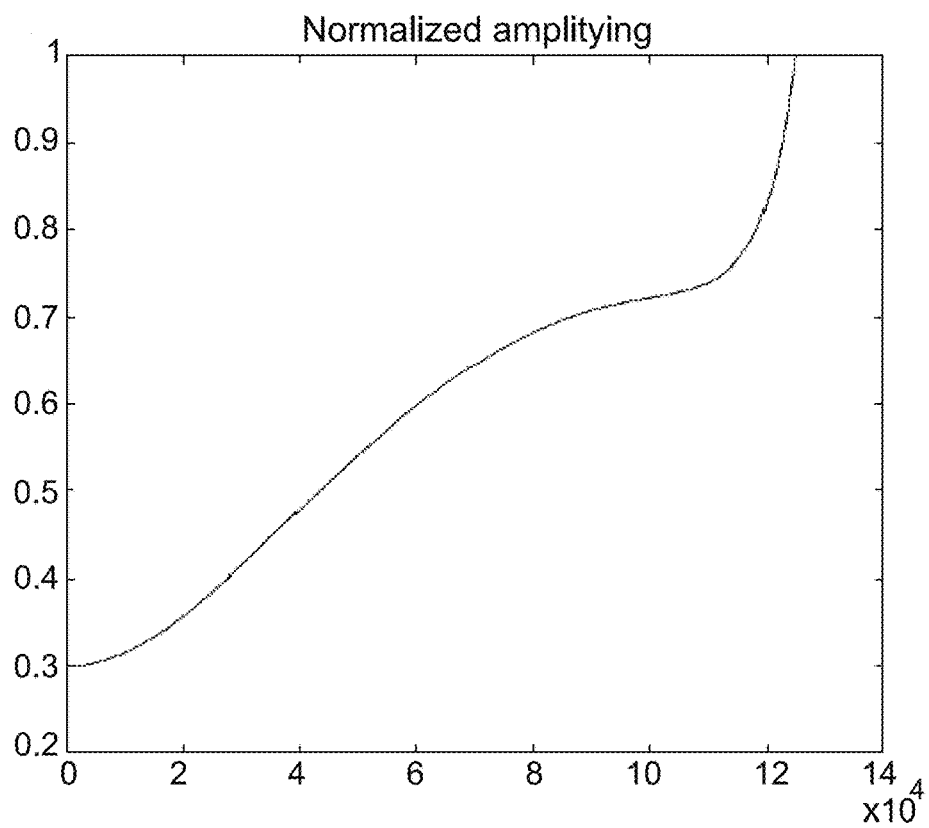
FIG. 7 shows calculated spectral gain provided by the 5321-illumination pattern.

Spectral harmonics of the piezoelectric sample ware measured and analyzed to determine gain and signal to noise ratio for each frequency. It should be noted that changes in modulation pattern of illumination also varies the intensity level of illumination, due to time of active illumination for each frame. For simplicity, the gain level is selected in accordance with first (low) harmonics as measured using the corresponding modulation illumination pattern, with respect to measurement using CW illumination (shown in FIG. 3). For example, FIG. 5 shows measured normalized SNR changes for the different harmonics (frequencies) using illumination pattern 5321 (including five ON tick, 3 OFF ticks 2 ON ticks and 1 OFF tick). It should be noted that in FIG. 5 and in the following figures, the first harmonic of 2 Hz is not shown due to normalization of the CW measurement with the patterned illumination measurement. FIGS. 6 and 7 show mathematical model of the gain provided by the selected pattern with respect to CW illumination. FIG. 6 shows normalized Sync function modulated by the 5321 pattern and by continuous CW illumination, FIG. 7 shows modeling of spectral gain provided by the 5321-illumination pattern. As shown, the mathematical model suits the experimental results of FIG. 5, providing increased gain to higher frequencies with respect to the lower frequencies.

Figure 8:
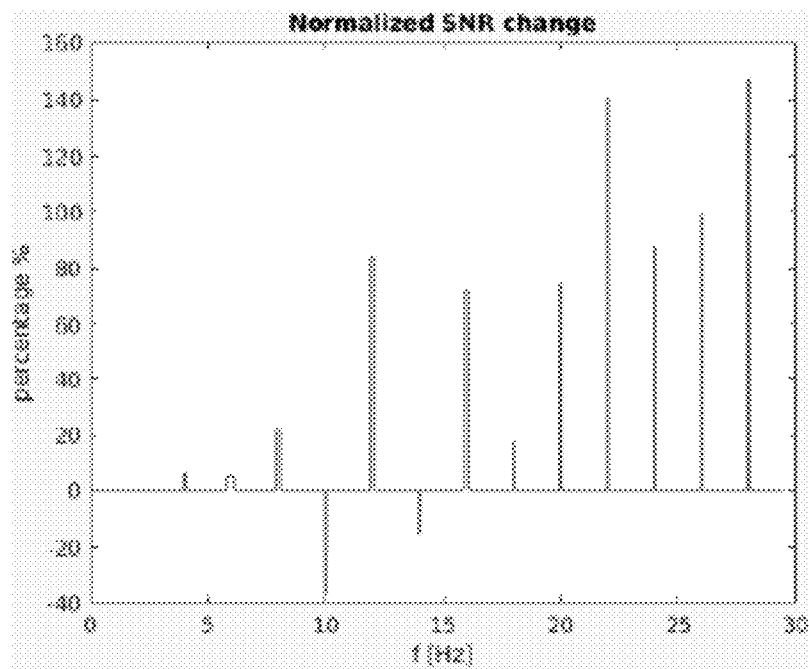
FIG. 8 shows experimentally measured normalized SNR changes for signal collection using illumination pattern A8532111.
Figure 9:
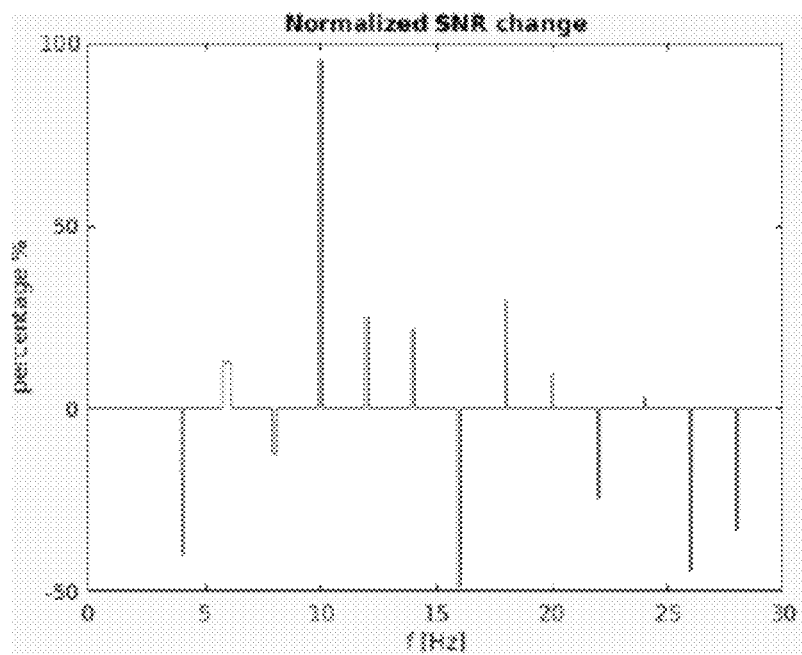
FIG. 9 shows experimentally measured normalized SNR changes for signal collection using illumination pattern 87755321.
Figure 10:
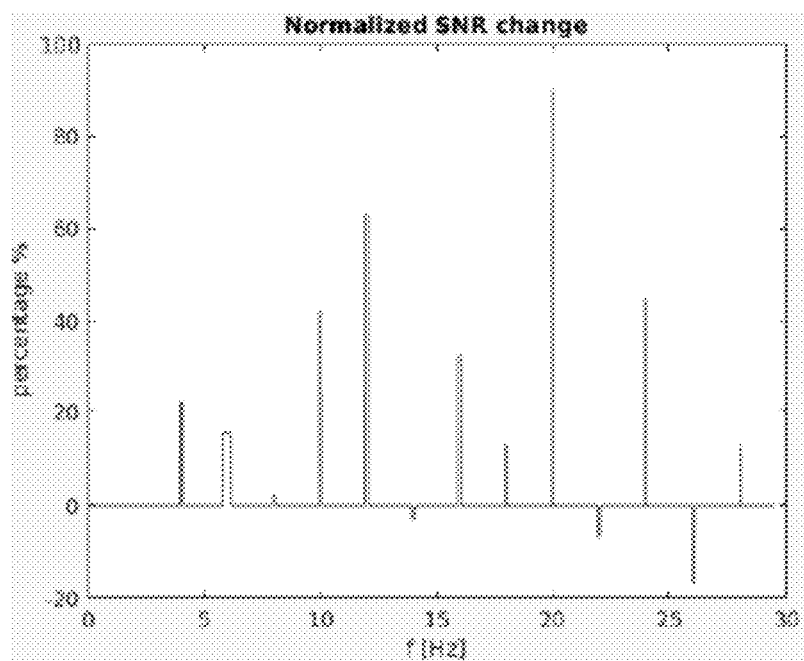
FIG. 10 shows experimentally measured normalized SNR changes for signal collection using illumination pattern 432111.

Generally, some illumination patterns provide increase in gain and SNR for the higher frequencies, while some other illumination patterns may provide limited increase or none at all. FIGS. 8-10 exemplify normalized gain changes for successful patterns (FIGS. 8 and 10) and unsuccessful pattern (FIG. 9). FIG. 8 shows normalized SNR changes measured using illumination pattern A8532111 (10 ON, 8 OFF, 8 ON, 3 OFF, 2 ON, 1 OFF, 1 ON, 1 OFF) providing enhanced gain of higher frequencies. FIG. 9 shows an example of illumination pattern 87755321 pattern showing increased gain in some frequencies but does not provide sufficient increase in the higher frequencies of over 20 Hz. More specifically, 87755321 pattern does not provide increased gain in high frequencies but rather decreases the gain in these frequencies. FIG. 10 shows another measured normalized SNR change in accordance with illumination pattern 432111. As shown this pattern provides increased gain in some (but not all) high frequencies, including specifically 10 Hz, 12 HZ, 20 Hz and 24 Hz. This result may be considered as limited success, moreover, as evident from the exemplary patterns shown here, actual selection of the illumination pattern may be determined in accordance with the desired frequencies for monitoring and the corresponding required gain.

Figure 11:
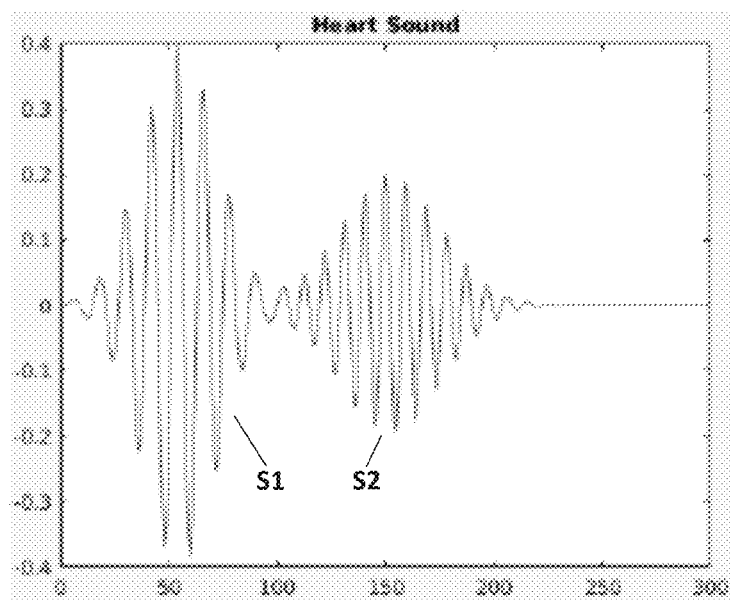
FIG. 11 shows heart bit pattern exemplifying S1 and S2 heart sounds.
Figure 12A:
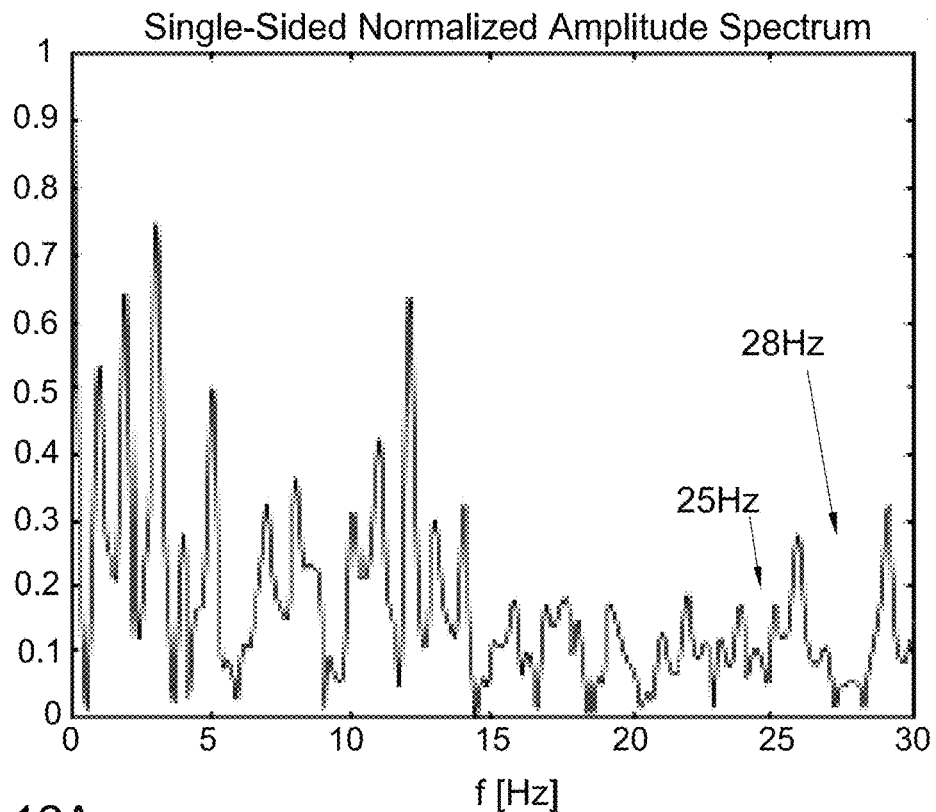
FIGS. 12A and 12B show normalized amplitude spectrum of heart rate signal measured with noise using CW illumination (FIG. 12A) and patterned illumination (FIG. 12B)
Figure 12B:
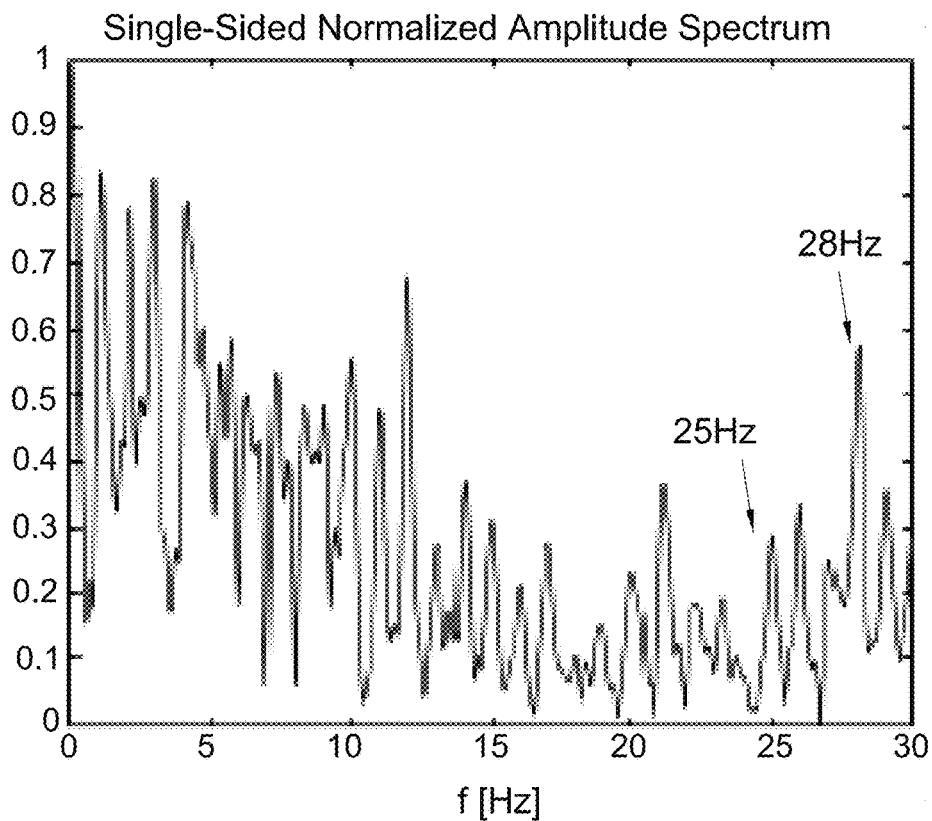
Figure 13A:
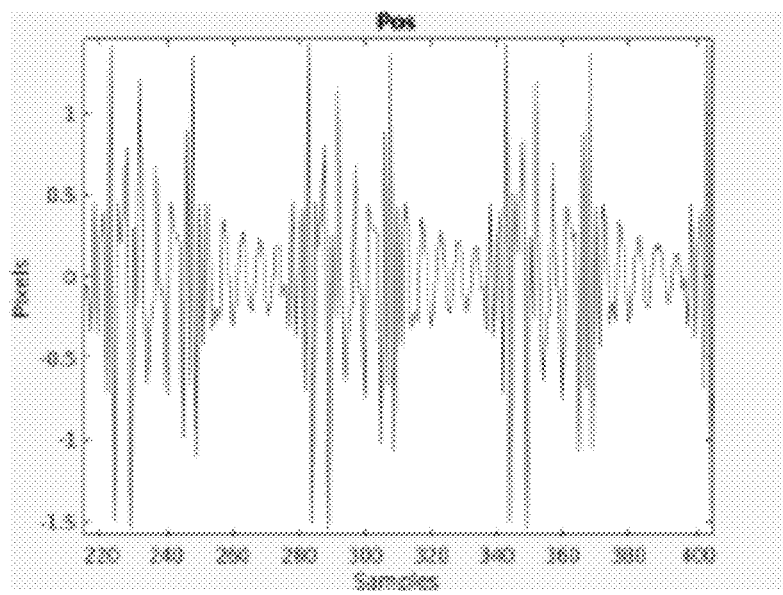
FIGS. 13A and 13B show corresponding POS reconstructed heart rate signals collected using CW illumination (FIG. 13A) and patterned illumination (FIG. 13B)
Figure 13B:
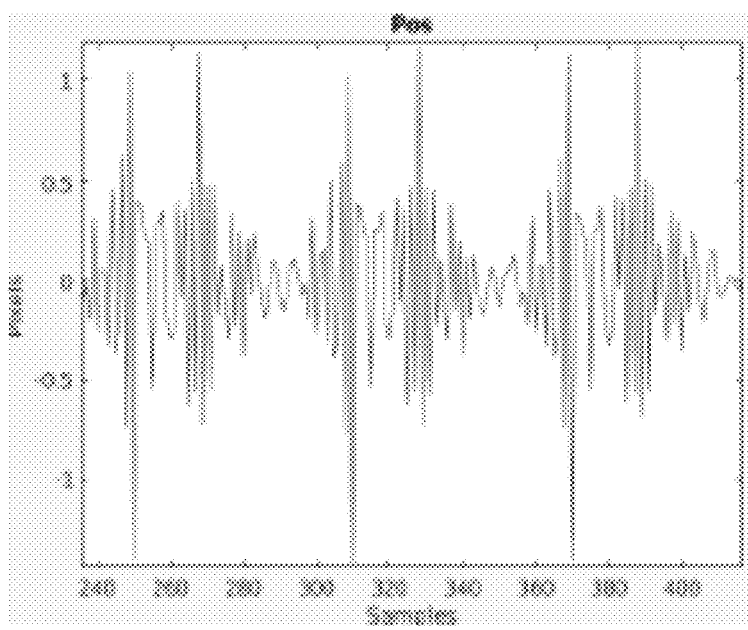
Figure 14A:
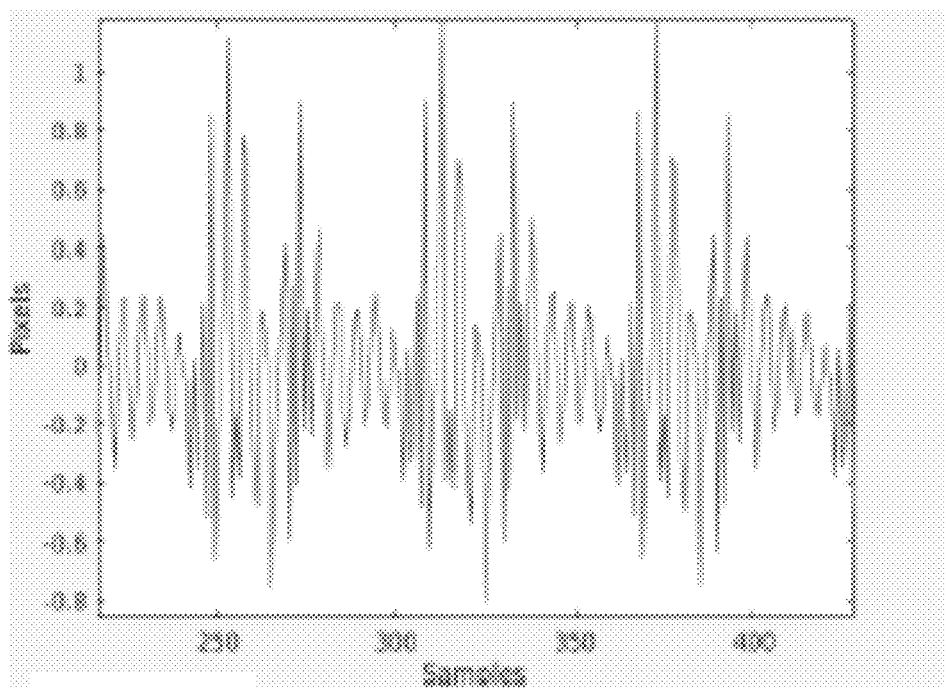
FIGS. 14A and 14B show DPOS reconstructed heart rate signals collected using CW illumination (FIG. 14A) and patterned illumination (FIG. 14B)
Figure 14B:
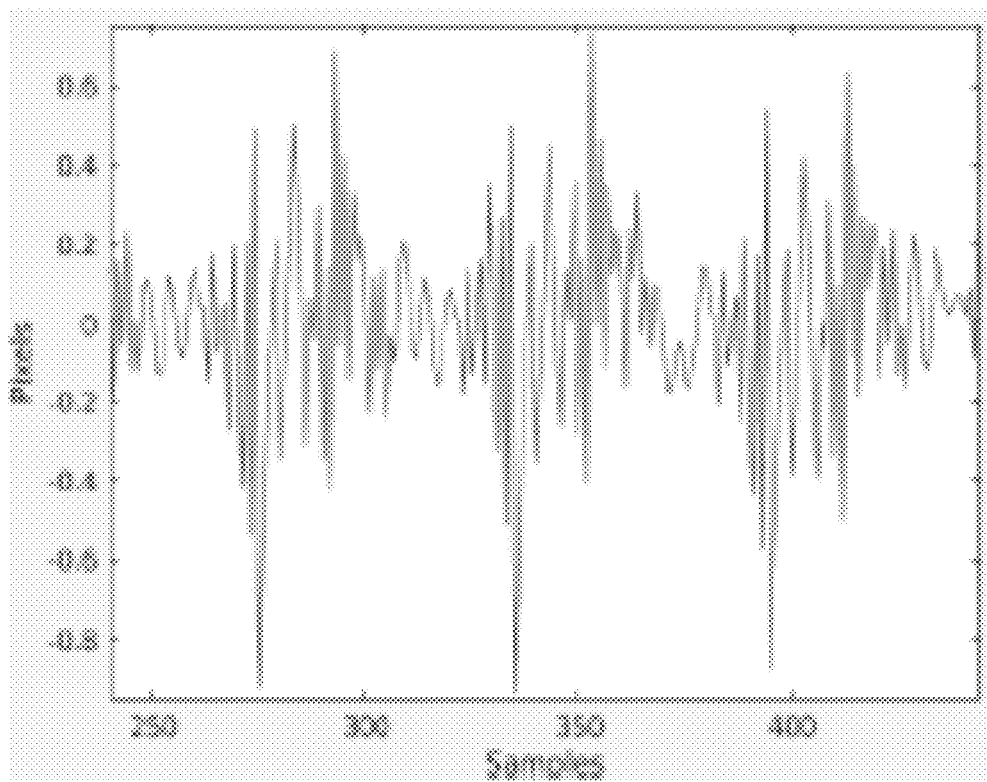

Additional experimental data was collected on a live patient. The system including light source (modulated 650 nm 5 mW continuous wave (CW) laser element) and imaging unit (Basler Camera) was positioned for monitoring heart activity of a test subject Reference is made to FIGS. 11, 12A-12B, 13A-13B and 14A-14B showing measurement results for heart beats of the subject. FIG. 11 shows reproduced experimentally measured heartbeat at frequency of 25 Hz, the horizontal (x) axis represents time in shifted units and the entire duration shown in FIG. 11 is 1 second (x axis from 1 to 300). As shown, the S1 and S2 amplitudes associated with ventricular and atrial contraction are shown within a time interval of 1 second. FIGS. 12A and 12B show normalized spectrum collected using CW laser illumination (FIG. 12A) and normalized spectrum collected using 532111 pattern (FIG. 12B). Specifically noted are the variations in gain at frequencies of 25 Hz and 28 Hz marked with arrows in FIGS. 12A and 12B, where the modulated illumination (FIG. 12B) provides increased gain over the CW illumination (FIG. 12A). FIGS. 13A and 13B show reconstructed heart rate signal using CW illumination and patterned illumination respectively. The heart rate data was reconstructed by determining spatial correlation between speckle patterns in consecutive frames and identifying position of the correlation peaks. FIGS. 14A and 14B show filtered reconstructed data of heart rate signal using CW illumination and patterned illumination respectively. In FIGS. 14A and 14B the detected heart rate signal was reconstructed by POS technique and further filtered by high pass filter to remove low frequency shifts of the correlation peak. In both reconstructions, S1 and S2 heart sounds are visible, while being better resolved when the modulated illumination patterns was used.

Figure 15:
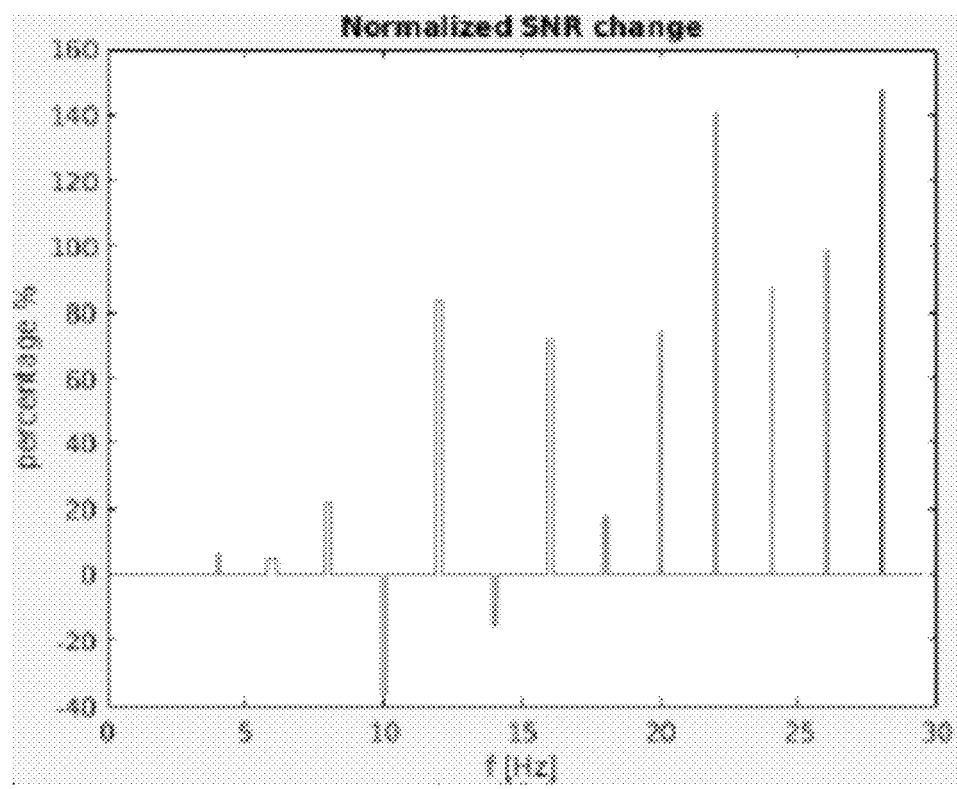
FIG. 15 shows normalized SNR change associated with using the 532111-pattern used for heart rate signal detection.

A general normalized SNR change achieved using the 532111 pattern is shown in FIG. 15 exemplifying the increase gain around frequencies of 22-28 as expected and desired for the heart rate measurement shown here.

Accordingly, the present technique utilizes modulated illumination pattern, in association with speckle-based monitoring technique for monitoring a sample with improved gain-frequency curve. More specifically, the present technique enables increasing the signal to noise ratio of selected frequencies, preferably higher frequencies within the sampling rate range, utilizing selected illumination pattern. It should be noted that selection of the illumination pattern may be determined in accordance with desired gain-frequency curve for a specific feature to be inspected. Further, as shown herein, with reference to FIGS. 5-7, there is high agreement between the experimental and calculated gain-curve enabling calculation of gain provided by selected patterns for optimizing the signal to noise of an inspection task.

Figure 16:
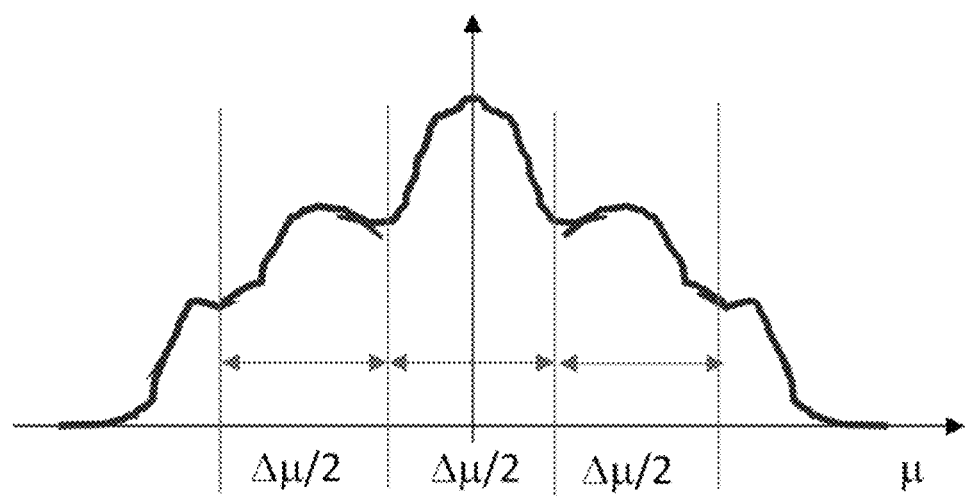
FIG. 16 exemplifies spectral slots of encoded pattern formed by sampling rate of a collection unit, each spectral slot is of width Δμ/2.

Utilizing additional embodiments of the present invention, the system may utilize a light source unit (e.g. 122 in FIG. 1) and pattern modulator (e.g. 124 in FIG. 1) configured for providing light modulation pattern selected to provide encoding pattern to different slots in the spectral (temporal frequency) domain, to thereby enable increase in sampling bandwidth. Accordingly, the present technique provides illumination modulation pattern having orthogonal codes of the frequency slots, with respect to convolution between the codes. Generally, and as also indicated above, sampling rate of the collection unit 140, or its detector array 142, result with effective digitation of the collected data when represented in the frequency domain. Reference is made to FIG. 16 exemplifying digitation into frequency steps of $\Delta\mu/2$ that is caused by the sampling rate of $1/\Delta\mu$ of the collection unit 140. This digitization of the data in frequency domain enables separation of the frequency domain into slots based on the sampling rate. According to this technique, the pattern modulator provides illumination modulation characterized by that the different slots of the temporal frequency domain are orthogonally modulated with respect to each other.

Accordingly, the pattern modulator 124 is typically be operated by the control unit 160 for selecting temporal modulation pattern c(t). The temporal modulation pattern c(t) is selected based on data on sampling rate of the detector array 142 such that in the temporal frequency domain, the modulation is $\hat{C}(\mu)$ and provides that sections of the modulation are orthogonal between them. More specifically, the modulation pattern c(t) is selected based on digitization of the frequency domain due to sampling rate of the detector array 142 to provide orthogonal coding between the different frequency slots. FIG. 16 exemplifies spectral/frequency slots having width of $\Delta\mu/2$ associated with sampling rate of $1/\Delta\mu$. Each spectral slot of the modulation pattern $\hat{C}(\mu)$ is denoted as $\hat{C}_m(\mu)$ and encoded with a pattern orthonormal to other spectral slots such that:

$$\hat{C}_m(\mu) * \hat{C}_n(\mu) = \begin{cases} 0 & \text{for all } n \neq m \\ 1 & \text{otherwise} \end{cases} \quad \text{(equation 1)}$$

Where $\mu$ refers to the temporal frequency, m and n are spectral slot index and $\hat{C}_m(\mu)$ is the modulation of spectral slot m as a function of frequency $\mu$ within the slot, the symbol * indicates convolution operation.

The selected coding allows for increasing bandwidth of signal collection. To this end the detector array is operated at the selected sampling rate $1/\Delta\mu$, for collecting one or more sequences of image data pieces indicative of secondary speckle patterns in interacting light, being light components interacting with from the inspection region R by being back scattered or transmitted through medium of the inspection region. As indicated above, the collection unit 140 includes an optical arrangement 144 positioned for collection of image data pieces of the inspection region R, thereby enhancing the secondary speckle pattern. As indicated above, the optical arrangement 144 and detector array 142 may be positioned for imaging of the inspection region while being in-focus or defocuses with respect to the inspection region. This may affect the preferred processing of the collected image data pieces for determining parameters of the inspection region.

The collected one or more sequences of image data pieces are send to the control unit 160 for processing and determining one or more parameters of the inspection region. The processing may include determining correlations between sequential speckle patterns in the image data piece (frames) to identify variation in spatial locations of the correlation peak and determine a time-correlation function. In some configurations, the processing may be associated by determining variation in contrast of the speckle patterns. In some additional configurations, the processing may include determining statistics of decorrelation between speckle patterns. Generally, the processing includes analysis of the speckle patterns within the sequence of image data pieces and determining at least one time-varying function indicative of variation of features in the inspection region. According to the present technique, the collected signal, or the time-varying function, is passed through a low pass filter (LPF) to filter out all frequencies above $|\Delta\mu/2|$ and thus remove noise of frequency that is higher than the sampling rate. In some embodiments, the low pass filter may be an optical element associated with the collection unit, however typically the low pass filter may be electronic using a low pass filter module of the control unit 160 operated on the time-varying function. The control unit 160 is generally configured as a computing unit including input and output ports, at least one processor and memory utility, and carried instructions for performing one or more selected processing operations as described herein.

Generally, given that the signal to be detected, associated with vibrations of the inspection region, is described in Fourier space by:

$$\sum_n \hat{S}_n\left(\mu - \frac{n\Delta\mu}{2}\right) \quad \text{(equation 2)}$$

and the Fourier of the modulated illumination signal is provided by:

$$\sum_m \hat{C}_m\left(\mu - \frac{m\Delta\mu}{2}\right) \quad \text{(equation 3)}$$

The collected signal in frequency domain (provided by Fourier of the time-varying function) is:

$$\hat{K}(\mu) \equiv \sum_n \sum_m \hat{S}_n\left(\mu - \frac{n\Delta\mu}{2}\right) * \hat{C}_m\left(\mu - \frac{m\Delta\mu}{2}\right) \quad \text{(equation 4)}$$

Due to sampling rate, defined herein as $1/\Delta\mu$, the modulation $\hat{C}(\mu)$ and signal $\hat{S}(\mu)$ are each separated into spectral sections $\hat{S}_n$ and $\hat{C}_n$, each having spectral width of $\Delta\mu/2$.

The illumination coding provides that different spectral slots of $\hat{C}(\mu)$ provide convolution code that is effectively multiplied with the signal s(t) in the time domain. This provides measured signals in the form of s(t)c(t), where s(t) is the temporal signal to be detected and c(t) is the temporal modulation of illumination, or in other words, the inverse Fourier transform of $\hat{S}$ multiplied by the inverse Fourier transform of $\hat{C}$. Thus, the spectrum of the collected signal $\hat{K}(\mu)$ is formed by a convolution of the illumination modulation and the signal to measure in the frequency domain as indicated in equation 4. It should be noted that since the illumination modulation pattern is real (and does not include imaginary illumination intensity), its Fourier representation $\hat{C}$ (the orthogonal spectral convolution code) is symmetric.

Due to the sampling rate of the collection unit 140, the collected signal $\hat{K}(\mu)$ includes replications in the spectrum with replication distance of $\Delta\mu$. The use of low pass filter on the collected signal filters out all frequencies above $|\Delta\mu/2|$ associated with the frequency range provided by the sampling rate. Accordingly, the collected signal can be described as:

$$\sum_l \hat{K}(\mu - l\Delta\mu) = \quad \text{(equation 5)}$$
$$\sum_l \sum_n \sum_m \hat{S}_n\left(\mu - \frac{n\Delta\mu}{2} - l\Delta\mu\right) * \hat{C}_m\left(\mu - \frac{m\Delta\mu}{2} - l\Delta\mu\right)$$

where based on the use of low pass filter, only the indexes that fulfill condition of frequency below the filter limit are registered. Thus only indexes that fulfill $$\left(\frac{n}{2}+l\right) - \left(\frac{m}{2}+l\right) = \begin{cases} 0 \\ -1/2 \\ +1/2 \end{cases} \quad \text{(equation 6)}$$

indicate registered frequency slot. This indicates a connection between signal and illumination frequency slot indexes as:

$$n = \begin{cases} m \\ m-1 \\ m+1 \end{cases} \quad \text{(equation 7)}$$

This is associated with the fact that the convolution between signal and illumination pattern $\hat{S}_n(\mu) * \hat{C}_m(\mu)$ has frequency range of $\Delta\mu$, which is twice the frequency range achievable based on sampling rate of the collection unit. Moreover, the use of orthogonal coding between frequency slots simplifies the collected signal leaving only frequency slots where m=K. Thus, the collected signal is indicative of the desired signal of the sample and can be represented as:

$$\hat{S}_K\left(\mu - \frac{K\Delta\mu}{2} - l\Delta\mu\right) + \hat{S}_{K-1}\left(\mu - \frac{K\Delta\mu}{2} - \Delta\mu - l\Delta\mu\right) + \quad \text{(equation 8)}$$
$$\hat{S}_{K+1}\left(\mu - \frac{n\Delta\mu}{2} + \Delta\mu - l\Delta\mu\right)$$

The use of low pass filter actually limits the summation to terms that fulfil:

$$\frac{K}{2} - l + \begin{cases} 0 \\ -1 \\ +1 \end{cases} = \begin{cases} 0 \\ -1/2 \\ +1/2 \end{cases} \quad \text{(equation 9)}$$

Resulting in measured data of the samples' signal within suitable frequency slots as:

$$\hat{S}_K(\mu) + \hat{S}_K\left(\mu + \frac{\Delta\mu}{2}\right) + \hat{S}_K\left(\mu - \frac{\Delta\mu}{2}\right) + + \hat{S}_{K-1}(\mu) + \quad \text{(equation 10)}$$
$$\hat{S}_{K-1}\left(\mu + \frac{\Delta\mu}{2}\right) + \hat{S}_{K-1}\left(\mu - \frac{\Delta\mu}{2}\right) + + \hat{S}_{K+1}(\mu) +$$
$$\hat{S}_{K+1}\left(\mu + \frac{\Delta\mu}{2}\right) + \hat{S}_{K+1}\left(\mu - \frac{\Delta\mu}{2}\right)$$

This collected data includes the complete measurement of the desire signal:

$$\hat{S}_{K-1}\left(\mu + \frac{\Delta\mu}{2}\right) + \hat{S}_K(\mu) + \hat{S}_{K+1}\left(\mu - \frac{\Delta\mu}{2}\right) \quad \text{(equation 11)}$$

Where the correct spectral slot K has frequency width of $\Delta\mu$. This desired information is already included in the measured data with additional measured elements associated with neighboring spectral slots.

To separate the desired terms of equation 11 out of the collected data (of equation 10), the control unit is typically operated for processing the collected data in accordance with data on the illumination encoding pattern. Generally, the processing may decode the data pieces associated with the highest spectral slot $K\Delta\mu$, determined by the sampling rate. More specifically, the processing may decode signal data pieces having index K value in which only $\hat{S}_{K-1}(\mu) \neq 0$ and $\hat{S}_K(\mu) = \hat{S}_{K+1}(\mu) = 0$, thereby determining $\hat{S}_{K-1}(\mu)$ data. This is followed by reducing the value of the spectral slot K by one and proceeding with the processing having two spectral slots different than zero. One of them computed in the previous session.

With each lower spectral slot providing two signal spectral slots that are not zero, thus allowing to determine the signal data, where one was determined with the higher spectral slot and the new, lower, encoded spectral slot is to be determined. This enable determined the encoded modulation using a ladder of spectral slots enabling detection of a desired signal with frequency band of $\Delta\mu$ with limited sampling rate.

Figure 17:
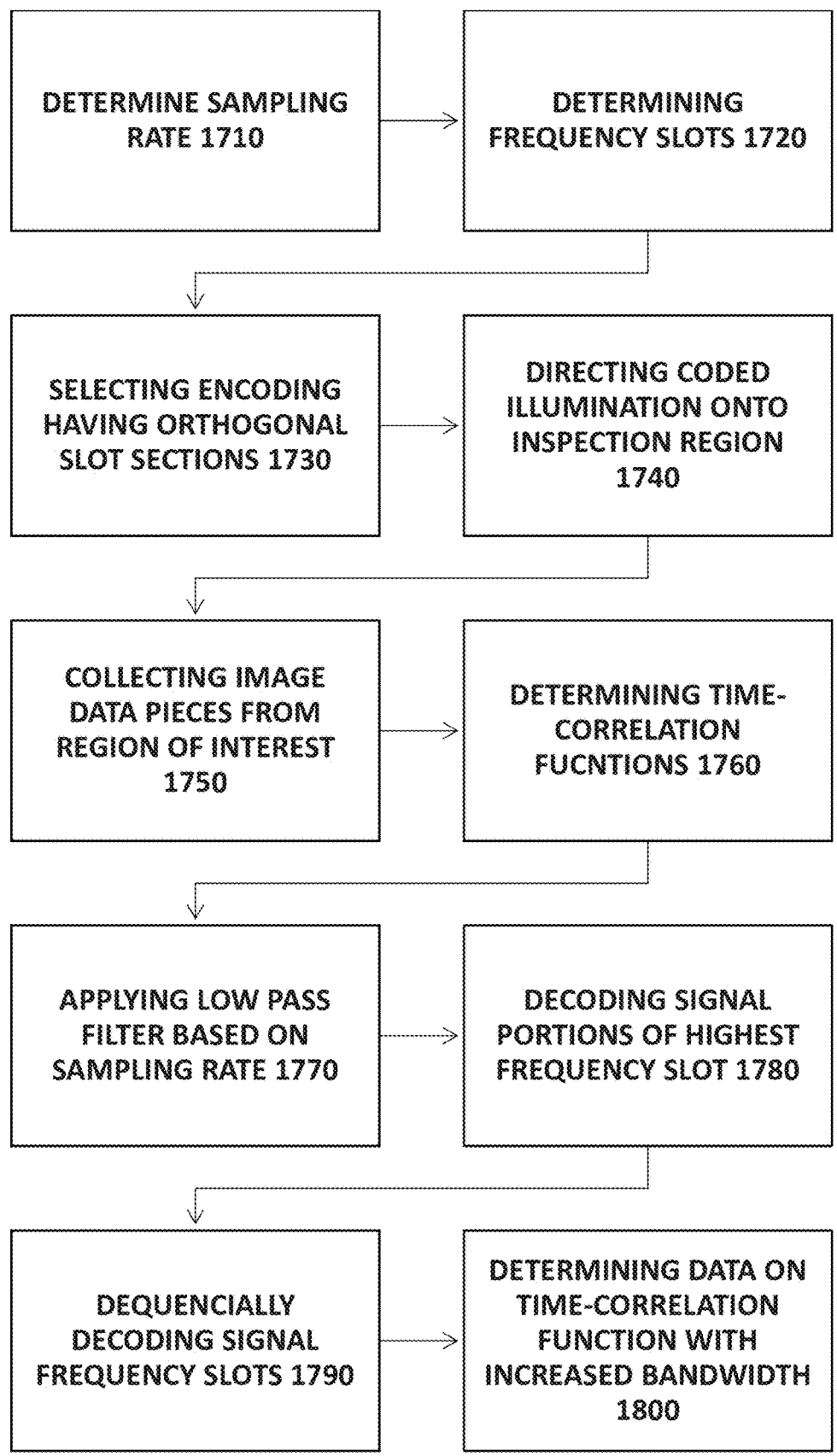
FIG. 17 is a flow chart illustrating a method for enhancing bandwidth for inspection of a sample according to some embodiments of the present invention.

The operation technique is further exemplified in FIG. 17, illustrating operation of the technique as described herein. As shown, the technique is based on data on sampling rate 1710 and determining corresponding frequency slots 1720 as exemplified in FIG. 16. Based on the frequency slots, an illumination encoding pattern is selected 1730 such that the different frequency slots of the encoding pattern are orthogonal to each other. Further, the technique includes illuminating the inspection regions 1740 with the encoded illumination pattern and collecting at least one sequence of image data piece 1750 at the selected sampling rate. The collected image data pieces are processed for determining a time-varying function 1760 indicative of the signal to be collected. Typically, the time-varying function is low pass filtered 1770 for removing noise and simplifying processing. Such low pass filter may be associated with relatively long exposure time for each frame or applying electronic low pass filter on the collected data (e.g. on the time-varying function). It should be noted that the time-varying function may generally be determined in time-domain, as variations in correlations between speckle patterns collected in image data pieces. The present technique may thus generally include determining a Fourier transform of the time-varying functions for further processing in the frequency domain. This may be performed after completing a collection section or after completing collection for a selected sampling window to provide semi-real time processing in moving window technique.

At this stage, the collected signal data, represented in Frequency domain, is ready for step by step decoding. As indicated above, due to the sampling rate, the signal and encoding pattern are formed in sections. Given the known encoding pattern, the processing decodes the signal slot portion of highest frequency index 1780. Further, as indicated above, each signal slot in decoded in turn based on previous signal slot 1790, until the entire frequency band is decoded. At this stage, the complete data of the collected signal is decoded and may be provided 1800, either in Frequency domain or transformed to time-domain as needed.

Thus, the present invention provides systems and methods allowing monitoring of parameters of a sample with improved temporal sampling associated with sampling of high frequency features and broadening sampling bandwidth. The present technique utilizes modulation of illumination providing pattern allowing increased sensitivity to selected (e.g. high) frequency signal portions, and in some configurations, extend the sampling bandwidth. The present technique improvs monitoring of sample parameters as compared to general illumination utilizing selected modulation pattern of illumination in accordance with desired gain increase curve and sampling bandwidth.

The invention claimed is:

1. A system comprising:
    an illumination unit comprising at least one light source configured for emitting coherent illumination of one or more selected wavelength ranges having selected illumination modulation pattern, and for directing said illumination onto one or more selected inspection regions, said illumination modulation pattern is characterized by a plurality of spectral slots associated with digitization by sampling rate of the collection unit, wherein said plurality of spectral slots are modulated to be orthogonal between them;
    a collection unit comprising at least one detector array and imaging optical arrangement configured for collecting interacting light from the one or more selected inspection regions and for generating corresponding one or more sequences of image data pieces at selected sampling rate, said image data pieces being indicative of secondary speckle patterns formed in collected interacting light;
    a control unit comprising at least one processor and memory utility and configured and operable for receiving said one or more sequences of image data pieces from the collection unit, determining at least one time-varying function indicative of variations between speckle patterns of different frames, said at least one time-varying function being indicative of variations of temporal features in the one or more inspection region;
    wherein said control unit is further configured for decoding said illumination modulation pattern, said decoding comprises: determining Frequency representation of the collected signal, identifying first signal portion associated with maximal frequency slot, utilizing prestored data on the illumination modulation pattern and decoding said first signal portion, identifying next signal portion associated with neighboring frequency slot, using orthogonality of the codes and prestored data on the illumination modulation pattern for decoding said next signal portion, maintaining said process for decoding the collected signal.

2. The system of claim 1, wherein said illumination modulation pattern comprises a selected arrangement of pulses providing at least one instance of zero amplitude portion within exposure time for collection of a corresponding image data piece by the collection unit.

3. The system of claim 1, wherein said illumination modulation pattern comprises pulse profile having repeating patterns comprises at least one zero intensity portion associated with exposure time for collection of a corresponding image data piece by the collection unit, said repeating pattern being aligned with sampling rate of said collection unit.

4. The system of claim 1, wherein said illumination modulation pattern comprises modulation of polarizing orientation of the coherent illumination directed toward said one or more selected inspection regions, said collection unit is configured and operable for collecting light of selected polarization orientation, such that modulation of polarizing orientation of the coherent illumination modulates intensity of collected light.

5. The system of claim 1, wherein said at least one light source is associated with at least one pattern modulator configured for modulating at least one of intensity and polarization of light emitted by the light source.

6. The system of claim 1, wherein said illumination modulation pattern comprises a binary sequence of ON and OFF illumination periods.

7. The system of claim 1, wherein said illumination modulation pattern comprises an intensity variation of illumination having at least three intensity levels, providing at least one temporal instance having zero illumination within frame of light collection.

8. The system of claim 1, wherein said imaging optical arrangement and at least one detector array of the collection unit are positioned for generating defocused image with respect to the one or more selected inspection regions.

9. The system of claim 1, wherein said imaging optical arrangement and at least one detector array of the collection unit are positioned for imaging of the one or more selected inspection regions in-focus.

10. The system of claim 1, wherein said plurality of spectral slots are modulated to be orthogonal between them with respect to convolution operation.

11. A method for use in monitoring a sample, the method comprising:
  (a) providing modulated illumination onto at least one inspection region on the sample, said modulated illumination comprises illumination of at least one wavelength range carrying temporal modulation, said modulated illumination is characterized by a plurality of spectral slots associated with digitization by sampling rate of the collection unit, wherein said plurality of spectral slots are modulated to be orthogonal between;
  (b) collecting interacting light from said at least one inspection region with a selected sampling rate and exposure time and generating at least one sequence of image data pieces associated with speckle patterns formed in the interacting light due to scattering by the sample;
  (c) receiving said one or more sequence of image data pieces, determining variations between speckle patterns of different frames and determining at least one time-varying function indicative of variations of temporal features in the one or more inspection region; and
  (d) determining frequency representation of the collected signal, identifying first signal portion associated with maximal frequency slot, utilizing prestored data on the illumination modulation pattern and decoding said first signal portion, identifying next signal portion associated with neighboring frequency slot, using orthogonality of the codes and prestored data on the illumination modulation pattern for decoding said next signal portion, repeating said process for decoding the collected signal;
  thereby enabling monitoring temporal variations in said samples with increased temporal bandwidth.

12. The method of claim 11, wherein said modulated illumination is in the form of pulsed modulated illumination comprising pulse train profile having repeating patterns, comprising at least one zero intensity portion associated with exposure time for collection of light for generating said image data pieces, said repeating pattern being aligned with said selected sampling rate.

13. The method of claim 11, wherein said modulated illumination comprises modulation of polarizing orientation of the coherent illumination directed toward said sample, and wherein collection of the interacting with light comprises filtering light of selected polarization orientation, such that modulation of polarizing orientation of the coherent illumination modulates intensity of collected light.

14. The method of claim 11, wherein said modulated illumination comprises a binary sequence of ON and OFF illumination periods.

15. The method of claim 11, wherein said modulated illumination comprises an intensity variation of illumination having at least three intensity levels, providing at least one temporal instance having zero illumination within frame of light collection.

16. The method of claim 11, wherein said plurality of spectral slots are modulated to be orthogonal between them with respect to convolution operation.

* * * * *